United States Patent [19]

Cooke

[11] 3,931,339

[45] Jan. 6, 1976

[54] REMOVAL AND NEUTRALISATION OF ACID CATALYST FROM PRODUCTS OF CUMENE HYDROPEROXIDE CLEAVAGE

[75] Inventor: Maurice Dudley Cooke, East Horsley, England

[73] Assignee: BP Chemicals International Limited, London, England

[22] Filed: Dec. 13, 1973

[21] Appl. No.: 427,021

[30] Foreign Application Priority Data

Jan. 11, 1973 United Kingdom................ 1531/73

[52] U.S. Cl............................................. 260/621 A
[51] Int. Cl.².................................... C07C 37/24
[58] Field of Search..................... 260/621 A, 621 C

[56] References Cited
UNITED STATES PATENTS

| | | | |
|---|---|---|---|
| 2,734,085 | 2/1956 | Adams et al.................. | 260/621 C |
| 2,737,480 | 3/1956 | Adams et al.................. | 260/621 A |
| 2,744,143 | 5/1956 | Filar............................... | 260/621 C |

OTHER PUBLICATIONS

Noller, "Chem. of Org. Comp.," pp. 551–552, (1965), 3rd edition.

Conant et al., "The Chem. of Org. Comp.," pp. 423–424, 4th edition, (1952).

*Primary Examiner*—Norman Morgenstern
*Attorney, Agent, or Firm*—Brooks Haidt Haffner & Delahunty

[57] ABSTRACT

The mineral acid catalyst is removed from the products of cumene hydroperoxide cleavage by contact with an aqueous solution of an inorganic salt and an excess of an alkali metal hydroxide or phenate in a first zone. Suitably the aqueous solution contains sodium sulphate and sodium hydroxide or phenate. The aqueous layer is removed and the organic layer contacted in a second zone with an aqueous solution comprising an inorganic salt and sufficient weak acid to decompose any phenate carried over from the first zone. Suitable weak acids are oxalic and citric acids but the preferred acid is carbonic acid formed 'in situ' by passing carbondioxide into the aqueous inorganic salt solution.

8 Claims, No Drawings

REMOVAL AND NEUTRALISATION OF ACID CATALYST FROM PRODUCTS OF CUMENE HYDROPEROXIDE CLEAVAGE

The present invention relates generally to a process for the production of phenol by the oxidation of cumene and mineral acid-catalysed cleavage of cumene hydroperoxide. In particular it relates to the removal and neutralisation of mineral acid catalyst and by-product organic acids from the cleavage products.

The production of phenol by the oxidation of cumene followed by the mineral acid-catalysed cleavage of cumene hydroperoxide is well-known. The cleavage product contains phenol and acetone as the principal products together with varying amounts of side-products in the form of tars and organic substances such as organic acids. Before the products can be recovered it is necessary to remove and neutralise the mineral acid catalyst and preferably the organic acids in the cleavage products since the presence of the acids in the subsequent distillation interferes with the efficient recovery of the products and by-products of the reaction in addition to causing corrosion of the distillation equipment. Hithertofore this has been achieved, for example, by treating the cleavage products with an aqueous solution of an inorganic salt to extract the acids and promote phase separation and an aqueous solution of an alkali metal hydroxide or phenate to neutralise the acids. Incomplete removal of the salts at this stage or the formation of an excess of alkali metal phenate results in their passing in the organic phase, either in solution or suspension, to the separation and purification stages where their presence leads to fouling of distillation column reboilers and product yield loss. A particularly damaging salt in this respect in sodium phenate which may be introduced in order to neutralise both the mineral acid catalyst and the organic acid by-products, thereby liberating phenol, or may be formed by the reaction of excess caustic soda, added as a neutralising agent, and phenol under alkaline conditions. The salts concentrate in the tar residues removed from various points in the process and eventually appear as ash when the tars are burned. High inorganic ash contents render the residual tar unsuitable for use as fuel oil to conventional boilers. In the past the tendency has been to attempt to maintain the pH slightly below 7.0 during the catalyst removal and neutralisation step in order to prevent alkali metal phenate being carried over to the subsequent washing step. In practice however difficulties are experienced during commercial operation in maintaining the pH slightly below 7.0 resulting in the aforementioned disadvantages. Moreover even if the pH is successfully maintained below 7.0 it is sometimes found that chemical losses, e.g. loss of methylstyrene, occur under acid conditions.

The present invention substantially overcomes the aforementioned disadvantages of the prior art by providing a process whereby the mineral acid catalyst and at least part of the organic acid by-products are removed and neutralised in such a manner that the cleavage products are not contaminated with undesirable quantities of inorganic or organic salts.

Accordingly the present invention is a process for the removal and neutralisation of mineral acid catalyst and organic acid by-products from the products of cumene hydroperoxide cleavage which process comprises contacting the products of the mineral acid catalysed cleavage of cumene hydroperoxide in a first zone with an aqueous solution comprising an inorganic salt and an excess of an alkali metal hydroxide or alkali metal phenate over the stoichiometric quantity required for neutralisation of the mineral acid catalyst and organic acid by-products whereby the acids are extracted from the organic phase into the aqueous phase and neutralised therein, separating the aqueous phase containing neutralised acids therefrom, further contacting the organic phase in a second zone with an aqueous solution comprising an inorganic salt and an acid in an amount sufficient to decompose alkali metal phenate carried over from the first zone and thereafter separating the aqueous phase therefrom.

The inorganic salt used in the first and second zones may be any water-soluble salt. Suitable salts include alkali metal sulphates such as sodium and potassium sulphate; ammonium sulphate; the alkali metal chlorides such as sodium and potassium chloride; ammonium chloride; and the alkali metal and ammonium phosphates and nitrates. However it is preferred to use a salt in which the anion corresponds to the anion of the mineral acid catalyst used in the cleavage reaction and the cation corresponds to the cation of the alkali metal compound used for neutralisation of the acid. Thus when sulphuric acid is the mineral acid and sodium hydroxide or sodium phenate the alkali metal hydroxide or phenate the preferred inorganic salt is sodium sulphate. In general concentrations of from about 0.5 up to about 50% by weight can be employed depending on the particular salt and temperature in use. With sodium sulphate for example a concentration between about 0.5 and 30% by weight and preferably of about 15 to 25% by weight at about 40° to 45°C is suitable for the removal of sulphuric acid.

The alkali metal hydroxide added to the first zone to neutralise the mineral acid catalyst and the organic acid by-products is preferably sodium hydroxide. Alternatively sodium phenate may be added to the first zone. The sodium phenate may be that sodium phenate resulting from the extraction of phenol from acetophenone at a later stage in the phenol-from-cumene-hydroperoxide process. Aqueous alkali metal hydroxide or phenate solution may be added to the first zone separately or combined with aqueous inorganic salt solution. It is preferred to combine the two solutions.

The amount of alkali metal hydroxide or alkali metal phenate added to the first zone must be greater than the stoichiometric quantity required to neutralise the mineral acid catalyst and the organic acid by-products but is preferably only sufficient to maintain the pH in the range 7 to 9.

The extraction and neutralisation of the acids in the first zone may be effected at any temperature up to about 50°C, though in general temperatures of about 35° to 45°C are preferred. The upper restriction on the temperature range is imposed by the desirability of avoiding plant corrosion and of avoiding precipitation of salt.

In addition to removing mineral acid catalyst in the first zone the treatment with an aqueous solution comprising an inorganic salt and excess of alkali metal hydroxide or alkali metal phenate also removes at least part of the organic acids present in the cleavage products, in the form of their alkali metal salts.

The acid contacted with the organic phase in the second zone is preferably a weak acid. By weak acid within the context of the present application is meant an acid of insufficient strength to cause corrosion of the plant and one which does not contaminate the organic phase with by-products. Suitable acids include oxalic acid and citric acid. The preferred acid is carbonic acid which may be formed 'in situ' by feeding carbon dioxide to the second zone in the presence of an aqueous solution of an inorganic salt in an amount sufficient to decompose the alkali metal phenate carried over in the organic phase from the first zone.

The aqueous solution of the inorganic salt the second zone may suitably be the aqueous p. pa- rated from the first zone. It is preferred hc to remove a part of the separated aqueous phase in a bleed stream in order to remove some of the sodium salts of organic acids from the system.

Contact of the aqueous solution with the organic phase in the second zone is suitably effected at ambient temperature but may be effected at any temperature in the range 10° to about 60°C., the temperature limits being dictated by the desirability of avoiding salt precipitation.

The following Example illustrates the process of the invention:

EXAMPLE

The products of the mineral acid catalysed cleavage of cumene hydroperoxide were treated in a first zone with a 20% by weight aqueous solution of sodium sulphate and sufficient aqueous sodium hydroxide solution to completely neutralise the sulphuric acid catalyst and organic acid by-products in the cleavage product and make the pH of the aqueous solution in the first zone in the range 7 to 8. The aqueous phase was separated and the organic phase free from acid, sampled for ash content before being passed to a second zone where it was washed with further aqueous sodium sulphate solution with simultaneous passage of an excess of carbon dioxide through the second zone. The aqueous phase was separated and the organic phase free from sulphuric acid, organic acids and sodium phenate tested for ash content prior to further processing. The results of the ash content analyses for varying concentrations of aqueous sodium sulphate solutions used in the second zone are shown in the Table.

| Concentration of $Na_2SO_4$ solution in 2nd zone % by weight | Dissolved ash before 2nd wash (ppm)* | Dissolved ash after 2nd wash (ppm)* |
|---|---|---|
| 0 | emulsified | |
| 5 | 850 | 60 |
| 20 | 850 | 10 |
| 20 | 320 | 25 |

*Ash contents were determined by ignition.

The results show that mineral acid catalyst and by-product organic acids are removed from the cumene hydroperoxide cleavage products by the process of the invention without contaminating the cleavage product with substantial quantities of residual salts.

I claim:

1. A process for the removal and neutralization of mineral acid catalyst and organic acid by-products from the reaction mixture resulting from mineral acid catalyzed cumene hydroperoxide cleavage which process comprises contacting at a temperature below about 50°C. said reaction mixture in a first zone with an aqueous solution comprising an acidic or neutral inorganic salt and an excess of alkaline alkali metal hydroxide or phenate sufficient to neutralize said mineral acid and organic acid by-products and to maintain the pH of the aqueous phase between 7 and 9 whereby said acids are extracted from the organic phase into the aqueous phase and neutralized therein, separating said aqueous phase containing the neutralized acids therefrom, then contacting at a temperature of from about 10°–60°C. said organic phase in a second zone with an aqueous solution comprising an acidic or neutral inorganic salt and a weak acid selected from the group consisting of carbonic acid, citric acid and oxalic acid in an amount sufficient to decompose alkali metal phenate carried over from the first zone, and thereafter separating the aqueous phase therefrom.

2. A process according to claim 1 wherein the acid is carbonic acid formed 'in situ' by feeding carbon dioxide to the second zone in the presence of an aqueous solution of an inorganic salt.

3. A process according to claim 1 wherein the inorganic salt is selected from alkali metal sulphates, ammonium sulphate, alkali metal chlorides, ammonium chloride, alkali metal phosphates, ammonium phosphate, alkali metal nitrates and ammonium nitrate.

4. A process according to claim 3 wherein the concentration of the inorganic salt is in the range 0.5 to 50%.

5. A process according to claim 1 wherein the inorganic salt used in the first and second zones in a salt in which the anion corresponds to the anion of the mineral acid catalyst used in the cleavage reaction and the cation corresponds to the cation of the alkaline alkali metal compound used for neutralisation of the acids.

6. A process according to claim 5 wherein the inorganic salt is sodium sulphate when sulphuric acid is the mineral acid catalyst and the alkaline alkali metal compound used for neutralisation of the acids is selected from sodium hydroxide or sodium phenate.

7. A process according to claim 6 wherein the concentration of sodium sulphate in the aqueous solution is in the range 0.5 to 30% by weight at a temperature in the range 40° to 45°C.

8. A process according to claim 1 wherein the alkaline alkali metal compound used for neutralisation of the acids is selected from sodium hydroxide and sodium phenate.

* * * * *

UNITED STATES PATENT OFFICE
CERTIFICATE OF CORRECTION

PATENT NO. : 3,931,339
DATED : January 6, 1976
INVENTOR(S) : MAURICE DUDLEY COOKE It is certified that error appears in the above–identified patent and that said Letters Patent are hereby corrected as shown below:

Col. 3, lines 10 to 13, the end of these lines were not printed, thus,
line 10, insert --used in-- after "salt"
line 11, insert --phase sepa-- after "aqueous"
line 12, insert --however-- after "preferred"
line 13, insert --phase-- after "aqueous"

Col. 4, line 34, after "zones" delete "in" and insert --is-- in lieu thereof.

Signed and Sealed this

Twentieth Day of July 1976

[SEAL]

Attest:

RUTH C. MASON
Attesting Officer

C. MARSHALL DANN
Commissioner of Patents and Trademarks